United States Patent [19]

Liberti

[11] Patent Number: 4,925,788

[45] Date of Patent: May 15, 1990

[54] IMMUNOASSAY SYSTEM AND PROCEDURE BASED ON PRECIPITIN-LIKE INTERACTION BETWEEN IMMUNE COMPLEX AND CLQ OR OTHER NON-IMMUNOSPECIFIC FACTOR

[75] Inventor: Paul A. Liberti, Churchville, Pa.

[73] Assignee: Immunicon Corporation, Huntingdon Valley, Pa.

[21] Appl. No.: 923,111

[22] Filed: Oct. 24, 1986

[51] Int. Cl.$^5$ .................. G01N 33/53; G01N 33/543; G01N 33/536; G01N 33/537

[52] U.S. Cl. ........................................ 435/7; 436/507; 436/509; 436/513; 436/518; 436/536; 436/538; 436/539; 436/541; 436/821; 436/824; 435/5

[58] Field of Search ............... 435/5, 7; 436/507, 509, 436/513, 518, 536, 538, 539, 541, 821, 824

[56] References Cited

U.S. PATENT DOCUMENTS 4,091,089  5/1978  Chichibu et al. ............... 436/805 X
4,283,383  8/1981  Masson et al. ................. 436/805 X
4,299,916 11/1981  Litman et al. ..................... 435/7 X
4,551,435 11/1985  Liberti et al. ..................... 436/541

Primary Examiner—Robert J. Warden
Assistant Examiner—Jack Spieger
Attorney, Agent, or Firm—Dann, Dorfman, Herrell & Skillman

[57] ABSTRACT

A test system and procedure for quantitatively assaying biological material for a target immunological substance by means of immunochemical binding of immune complexes, comprising the target substance and its immunospecific conjugate, to insolubilized non-immunospecific factor, such as Clq. A sample of biological material suspected of containing the target substance is introduced into the test system including pre-determined amounts of the target substance and its immunospecific conjugate forming immune complexes having a known degree of chemical binding to the non-immunospecific factor. The amount of target substance present in the test sample is determined according to the deviation from the known degree of immunochemical binding caused by the addition of the sample to the test system, by reference to a standard curve.

46 Claims, 4 Drawing Sheets

IMMUNOASSAY SYSTEM AND PROCEDURE BASED ON PRECIPITIN-LIKE INTERACTION BETWEEN IMMUNE COMPLEX AND CLQ OR OTHER NON-IMMUNOSPECIFIC FACTOR

BACKGROUND OF THE INVENTION

The present invention relates to the field of immunoassay techniques for the detection and determination of immunologically active substances in biological specimens and in particular to a novel test system and procedure for performing quantitative immunoassays and to processes for preparing the test system and carrying out the procedure.

A number of different types of immunoassays are currently in use for the detection, identification and quantitation of immunologically determinable substances, e.g. antigens and antibodies, in various biological materials. In carrying out an immunoassay, a labeled, immunoreactive substance is employed either directly or conjugate, by means of an immune reaction between the two substances. Even substances that are not immunogenic by themselves, such as haptens, can be determined by immunoassay if they are bound to a macromolecular carrier capable of inducing antibody to the lower molecular weight substance. Immunoassays are useful in determining the occurrence of immune reactions in blood serum, e.g. for monitoring and/or detecting infectious diseases, and are also widely used in a number of immunohistochemical methods performed on tissue. Recent advances in immunoassay techniques involving in vitro testing of minute levels of host antibody response to an infectious agent have become the method of choice for the detection of infectious disease.

Immunoassays may be carried-out either in solution, or on various solid supports to which the immunologically determinable substance or its immunospecific conjugate is affixed. As between the two, the latter procedure, known as solid-phase immunoassay, is preferred in practice because of its simplicity of performance and the ease with which the immune complexes formed on the solid phase may be separated from unreacted antigen or antibody.

One commonly used type of solid-phase immunoassay involves a non-competitive binding technique for determination of antigen or antibody. In performing an immunoassay of this type for the determination of antibody, antigen is immobilized on a solid support and then contacted with the test specimen suspected of containing the antibody of interest. Thereafter, a second labeled antibody that reacts specifically with the antibody of interest is added to the sample. Because the second antibody is labeled, the presence of the antibody of interest can be determined. By means of this technique, commonly known as the "sandwich" or "second antibody" technique, specific antibody can readily be detected in blood serum, for example. The radioallergosorbent test (RAST) for the measurement of specific IgE antibody to a variety of allergens is based on this procedure, as are assays for the measurement of antibodies to a number of infectious agents, such as hepatitis B, rubella, influenza and human T-cell lymphotropic virus III (HTLV III), the virus apparently responsible for Acquired Immune Deficiency Syndrome (AIDS).

In certain cases, the "sandwich" technique may be modified to include one or more additional layers of antigen or antibody to increase the sensitivity of the assay, or to permit the detection of antibody to antigens that are not easily attached to a solid surface.

Solid-phase immunoassays are also performed as competitive binding assays, based upon competition between labeled and unlabeled forms of an immunologically determinable substance for binding sites on the immunospecific conjugate. For example, in order to determine the amount of antibody present in a biological specimen using a competitive assay, a test sample is mixed with labeled antibody, and then contacted with the corresponding antigen bound to a solid support, with any unlabeled antibody present in the sample competing with labeled antibody for antigen binding sites or determinants. The test sample is then separated into a liquid-phase and a solid-phase and the relative amount of labeled antibody present in either phase is determined. Most competitive binding assays operate on the principle that any immunologically determinable substance present in the test sample and a labeled form of the same substance will be attracted with essentially equal affinity to a solid support bearing the immunospecific conjugate. Therefore, the labeled and unlabeled forms of the immunologically determinable substance become bound to the support in amounts proportional to the relative amounts of each substance present in the test sample.

Radioactively labeled reagents have been employed for some time in the above-described immunoassays, because of the sensitivity and accuracy of the assays employing such reagents. The radioisotope labels provide a readily measurable signal which permits the results of the assay to be determined directly. More recently, enzyme-labeled reagents have been widely used in immunoassays. In performing an immunoassay using an enzyme-labeled reagent, the enzyme activity of one of the separated portions of the test sample is measured by incubating the appropriate fraction with a substrate for producing an enzyme-catalyzed reaction, typically involving production or extinction of a colored compound whose adsorption may be readily measured either qualitatively or quantitatively. Such assays are reported to be comparable to the radioassays in sensitivity and offer certain operational advantages over radioimmunoassay techniques. Various chromophoric materials, such as fluorescent or phosphorescent substances are also commonly employed as labels in the above-described immunoassays.

If quantitation of an immunologically determinable substance is desired in carrying out an immunoassay, a standard curve is constructed from data gathered from a pre-determined number of samples, each containing the same known concentration of a labeled form of the immunologically determinable substance and various known concentrations of unlabeled immunospecific conjugate. The samples are incubated, any free immunologically determinable substance is separated from that which is bound or complexed with the immunospecific conjugate, and then, by use of an appropriate detector, the percent of either the free or bound labeled immunologically determinable substance, or both, is determined. This procedure is repeated for all of the samples and the percent of bound labeled immunologically determinable substance is plotted as a function of the concentration of immunologically determinable substance. Typically, as the total concentration of immunologically determinable substance increases, the relative amount of the labeled form thereof bound to the immunoreactive conjugate decreases. Once the standard curve is prepared, it is thereafter used to determine the concentration of immunologically determinable substance of interest in test samples undergoing analysis.

In the above-described solid phase immunoassays, for each immunologically determinable substance sought to be determined, the corresponding immunospecific conjugate, in purified form, is required for preparation of the solid phase. Thus, each solid phase reagent can be used for detection of a single immunoreactive substance, and for no other substance. Furthermore, the methodology involved in the prior art immunoassays generally requires two or more adsorption steps, each of which entails washing of unbound immunoreactive substance and incubation. The number and nature of the process steps employed in the immunoassays of the prior art tend to adversely affect the quantitative reliability of the results obtained thereby.

The development of an immunoassay for the determination of immunologically determinable substances in a more efficient manner with greater quantitative reliability than the procedures heretofore available remains a highly desirable objective. This is particularly true with respect to the detection and/or monitoring of infectious diseases based on a determination of a host's production of antibody in response to the infectious agent.

SUMMARY OF THE INVENTION

It has now been discovered that notable improvements in efficiency and quantitative reliability in the determination of immunologically active substances are achievable in accordance with the present invention, which effectively involves a new immunoassay principle. In accordance with one aspect of the present invention, there is provided a process for preparing an immunoassay for quantitatively assaying a biological fluid for an immunological substance by means of immunochemical binding of immune complexes, which are composed of the immunological substance and its immunospecific conjugate, to non-immunospecific factor having binding affinity for such complexes. The term "non-immunospecific factor" used herein includes, for example, Clq (the antibody-binding portion of the first component of complement), rheumatoid factor (RF), rheumatoid factor-like antibody, and Fc receptors or Fc receptor-bearing cells, with Clq being preferred. As used herein, the term "bimmunological substance" refers to either antibody or antigen and the term "immunospecific conjugate" refers to those substances reacting specifically with an immunological substance. Thus, if the immunological substance sought to be determined is antibody, the immunospecific conjugate would be the antigen which reacts specifically with that antibody, and vice versa. The term "antibody", as used herein, includes serum proteins, generally referred to as immunoglobulins, as well as monoclonal antibodies.

The immunological substances Which may be assayed according to this invention are those forming a complex lattice with their immunospecific conjugate when interacting at immunological equivalence. The binding of such complexes to insolubilized non-immunospecific factor is a function of the composition of the complexes which may be conveniently represented by an immunoprecipitation-like binding curve, established over a range of compositions of immune complexes, which range includes compositions in which the amount of the immunological substance to be determined (hereinafter sometimes referred to as the target substance) and the amount of immunospecific conjugate are in substantial equivalence, compositions in which the amount of the immunological substance is in substantial excess of the amount of said immunospecific conjugate, and compositions in which the amount of immunospecific conjugate is in substantial excess of the amount of the immunological substance.

In preparing the immunoassay, a test device is first provided comprising the non-immunospecific factor in insolubilized form, e.g. affixed to a solid carrier or support. Selected working limits for the assay are then established within the aforesaid range of compositions of the immune complexes. Next, a standard assay curve is constructed by plotting the relative degree of immunochemical binding of the immune complexes to the test device, with the immune complexes being formed in a reference system comprising varying concentrations of the target substance and a fixed concentration of its immunospecific conjugate, so that the composition of the resulting complexes is within the selected working limits determined in the preceding step. A test system is thereafter provided, comprising the test device, the immunospecific conjugate and the target substance, in which the amount of the conjugate is substantially equivalent to the above-mentioned fixed concentration thereof and the amount of the target substance is appropriate to produce a known degree of immunochemical binding, corresponding to a pre-determined point on the standard assay curve. This test system, prepared as just described, enables efficient and reliable quantitative assaying of the target substance in biological materials, such as blood serum, urine, cystic fluid and cerebrospinal fluid.

In accordance with another aspect of the present invention, there is provided a process for assaying a biological material for a target substance, using the immunoassay prepared as described above, which includes the steps of adding a sample of biological material, suspected of containing the target substance to the above-described test system; measuring any deviation from the known degree of immuno-chemical binding caused by the addition to the test system of any target substance present in the test sample; and determining the amount of target substance present in the biological fluid undergoing assay, based on the deviation from the known degree of immunochemical binding measured in the measuring step, by reference to the standard curve.

The above-described process may beneficially be carried out for the determination of multivalent antigen by competitive assay, using a test system comprising the target substance and its immunospecific conjugate in amounts such as to form immune complexes, the composition of which is within the zone corresponding to substantial equivalence between the target substance and its immunospecific conjugate on the standard assay curve. The degree to which immunochemical binding of appropriately labeled immune complexes to the test device is decreased by the presence of any antigen in the sample added to the test system, as indicated by the relative amount of label then present on the test device, provides the measure of deviation from the previously established known degree of immunochemical binding.

Assays for multi-determinant antigens may be facilitated by using a defined mixture of antibodies directed against individual determinants and of equal binding affinity and concentration. Monoclonal antibodies may be used to advantage for this purpose.

The immunoassay of the invention may also be employed to advantage in the determination of antibody. In one such assay, a test system is employed containing an amount of immunospecific conjugate that constitutes an excess relative to the target substance, for the lowest level of target substance which is capable of binding to the test device, when present with a substantially equivalent amount of the immunospecific conjugate. Alternatively, a test system may be used comprising immunospecific conjugate and target substance in amounts such as to form immune complexes, the composition of which is within the region of the standard assay curve wherein the immunospecific conjugate is in substantial excess of the target substance. In either case, the degree to which immunochemical binding of appropriately labeled immune complexes to the test device is increased by the presence of any antibody in the sample added to the test system, provides the measure of deviation from the previously established known degree of immunochemical binding. The degree of increase is indicated by the relative amount of label determined to be present on the test device. This aspect of the invention is especially suited for the determination of complement-fixing antibody using Clq as the non-immunospecific factor.

In accordance with a further aspect of the present invention, there is provided a process for preparing an immunoassay for quantitatively assaying biological material for monovalent bindable substance (hereinafter referred to as "bindable substances") by means of inhibition of coupling of formed complexes to the above-mentioned non-immunospecific factor. In this aspect of the invention, the formed complexes are composed of a multivalent form of the bindable substance and a multivalent binding partner which has specific binding affinity for, and binds to, the bindable substance. Here again, the degree to which the formed complexes comprising the multivalent form of bindable substance and its multivalent binding partner binds to the non-immunospecific factor is a function of the composition of the formed complexes, which may be represented by an immunoprecipitation-like binding curve, constructed over the range of compositions of the complexes previously noted.

The term "bindable substance", as used herein, refers to haptens and other low molecular weight substances which react selectively with particular proteins having a specific binding affinity for such substances. Haptens are protein-free substances that are non-antigenic by themselves, i.e. do not stimulate antibody formation, but react selectively with specific antibodies. For the formation of anti-hapten antibodies, the hapten is coupled to a high molecular weight substance, usually a protein, and injected into a test animal, after which the antibody is isolated in the usual manner.

The process for preparing the immunoassay for bindable substances is quite similar to that for immunological substances described above. Thus, a test device comprising insolubilized non-immunospecific factor is provided and the selected working limits of the assay are established within the above-mentioned range of compositions of formed complexes. A standard assay curve is constructed by plotting relative degree of coupling of the formed complexes to the test device, employing a reference system comprising a fixed concentration of each of the multivalent form of the bindable substance and the multivalent binding partner, and varying concentrations of the bindable substance. The relative concentrations of the multivalent form of the bindable substance and the multivalent binding partner should be such that the composition of the formed complexes is within the selected working limits of the formed complexes previously determined. In this process also, a test system is provided, comprising the test device, the multivalent binding partner, the multivalent form of the bindable substance and the bindable substance itself, the respective amounts of the former two reagents being substantially equivalent to the above-mentioned fixed concentrations thereof, and the amount of the bindable substance being appropriate to produce a known degree of coupling, corresponding to a predetermined point on the standard assay curve.

In accordance with yet another aspect of this invention, there is provided a process for assaying biological material for bindable substance, using the above described immunoassay. The assay for bindable substance, like that for immunological substances, involves the steps of adding a sample of the biological material suspected of containing the bindable substance to the above-described test system, including the test device, the multivalent form of the bindable substance and the multivalent binding partner; measuring any deviation from the known degree of coupling caused by the addition to the test system of any bindable substance present in the test sample; and determining the amount of bindable substance present in the biological material undergoing assay, based on the deviation from the known degree of coupling measured in the measuring step, by reference to the standard curve. For example, in performing a hapten determination using the assay of the invention, a test system is used preferably comprising, in addition to an appropriate amount of the hapten sought to be determined, as previously noted, a multivalent form of the hapten and antibody which binds specifically thereto, in amounts such as to form complexes whose composition is within the region corresponding to substantial equivalence between the multivalent form of the hapten and its specific binding antibody on the standard assay curve. In this assay also, the degree to which coupling of appropriately labeled formed complexes to the test device is decreased by the addition of the sample to the test system provides the measure of deviation from the already established known degree of coupling. The degree of decrease is indicated by the relative amount of label determined to be present on the test device.

Procedures based upon the new immunoassay principle described above offer distinct advantages over the immunoassay procedures heretofore available, particularly as applied to antibody determinations. For example, the assay of the invention eliminates the requirement that an antibody determination for a specific infectious viral agent utilize its own viral protein adsorbent. This is because the non-immunospecific factor component of the test device exhibits affinity for immune complexes generally, rather than for any given immunospecifically recognizable component thereof. According to the present invention, antibody may be quantitatively or qualitatively determined simply by incubating an appropriate quantity of labeled antigen with a test sample in the presence of insolubilized non-immunospecific factor, such as Clq. Thus, the assay of the invention is universally applicable to a variety of different immunological substances and monovalent bindable substances, without having to modify the test device. Another practical advantage of the immunoassay of the invention is that the processing time and number of manipulative steps involved is about one-half of that required in immunoassay techniques currently in use.

Another significant advantage is that the assay of the invention enables reliable quantitation of nanogram quantities of immunological substances and monovalent bindable substances present in a variety of biological materials.

BRIEF DESCRIPTION OF THE DRAWINGS

The novel features and advantages of the present invention are described more fully hereinbelow, with reference to the accompanying drawings, in which:

FIGS. 1 and 2 graphically represent an antigen test system for determination of IgE, according to the present invention. Specifically.

FIGS. 3–5 graphically represent an antibody test system for determination of rabbit anti-peroxidase, according to this invention. Specifically, FIG. 4.

FIGS. 6 and 7 graphically represent a hapten test system for determination of dinitrophenol, according to the present invention. Specifically.

The detailed description of the invention provided below focuses primarily on determinations of immunological substances. It is to be understood that whatever is stated with respect to immunological substances generally applies to bindable substances as well.

DETAILED DESCRIPTION OF THE INVENTION

The present invention is based on a number of related discoveries regarding interactions of specifically formed immune complexes with various non-immunospecific factors. It has been found that when a quantity of immunological substance and its immunospecific conjugate interact at a level which is insufficient to form a precipitating complex, soluble complex which is formed binds to insolubilized or solid phase non-immunospecific factor, such as Clq. It has also been discovered that when variable amounts of an immunological substance are complexed with a fixed amount of its immunospecific conjugate, and the relative amount of the immune complex thus formed, which becomes bound to the solid phase non-immunospecific factor, is plotted as a function of the varying concentrations of immunological substance, the resultant curve mirrors the well-known precipitation curve. That is to say, the degree of interaction between the complexes and the non-immunospecific factor is greatest when the ratio of immunological substance to its immunospecific conjugate is substantially equivalent.

Two phenomena are believed to be responsible for the observed binding affinity of formed immune complexes for solid phase non-immunospecific factor. First, as the concentration of immunological substance in the system increases, the formed immune complexes grow in size to some maximum level and then decreases to a point at which each molecule of immunospecific conjugate, e.g. antibody, is saturated with immunological substance, e.g., antigen. It has now been shown experimentally that as the relative quantity of immunological substance in the formed complex increases, a level is reached at which the complex no longer binds to solid phase non-immunospecific factor. These stages of the growth and decline in immune complex size correspond generally to the areas of antibody excess, equivalence and antigen excess on a precipitation curve. Second, the composition of immune complex formed at each incremental addition of immunological substance is different. In the case of antigen/antibody interactions, for example, different ratios of antigen and antibody exist within the complex, depending on the amount of antigen present in solution. In this connection, it has been experimentally demonstrated that when a given level of antibody is equilibrated with antigen, in antibody excess, after which additional antigen is added, and the mixture allowed to interact with solid phase Clq, the amount of immune complex bound to Clq is quantitatively identical to the amount that would have been bound had the total antigen been added initially. This result surprisingly shows that at the soluble immune complex concentration level, antigen-antibody immune reactions rapidly re-equilibrate. The outcome of this experiment also tends to indicate that the formed immune complexes are sufficiently small that ratio reequilibration between antigen and antibody also occurs. Thus, it would appear to follow that immune complex composition, and perhaps size, plays a significant role in the immunochemical binding of immune complex to solid phase non-immunospecific factor.

The above-noted discoveries have been put to practical application in the immunoassay of this invention, which is useful in testing for a variety of immunologically active substances. Representative examples of these substances are antigens, such as IgE, complement components, albumin and ferritin, as well as viruses, virus capsids, virus subunits, and protein hormones; haptens such as theophylline, phenytoin, primadone, cyclosporine, thyroid hormones, adrenocorticotrophic hormone (ACTH), cortisol, estrogen, testosterone, angiotensin, digoxin, penicillin, vitamin $B_{12}$ and intrinsic factors; and low molecular weight substances such as prolactin and gastrin. The assay of the invention is especially useful for the detection of antibodies to HTLV III, rubella, chylmidia, influenza and hepatitis B.

The test device utilized in the practice of the invention comprises non-immunospecific factor immobilized on a solid support. The non-immunospecific factor component of the test device is characterized by having affinity for immune complexes comprising aggregated antibody, but essentially no affinity toward non-aggregated antibody. The expression "aggregated antibody", as used herein, refers to an antibody which has undergone immune reaction with antigen giving rise to an immune complex in which the antibodies are clustered in a relatively dense mass. As such, "aggregated antibody" is to be distinguished from "non-aggregated antibody", which is antibody that effectively is in an immunologically unreacted state, or antibody that has undergone an immune reaction with an antigenic substance that has only a small number of determinants and thus forms an immune complex that does not include antibody clusters.

There are a number of naturally occurring substances which exhibit affinity for aggregated antibody, including Clq, rheumatoid factor, rheumatoid factor-like antibody, Fc receptors or Fc receptor-bearing cells. These non-immunospecific factors will bind to most immunoreactive substances provided they produce, or can be caused to produce an immune complex comprising aggregated antibody, upon reaction with their respective immunospecific conjugates. It should be noted, however, that when Clq is employed as the non-immunospecific factor in an assay involving non-complement-fixing antibody, the latter must be modified by complexation with complement-fixing antibody, so that complement-fixing antibody will be present in the immune complex formed in carrying out the assay. Similar modifications may be necessary when rheumatoid factor, rheumatoid factor-like antibodies, Fc receptors or Fc receptor cells are used as the non-immunospecific factor.

When using rheumatoid factor as the non-immunospecific factor, it should be possible to apply the assay of the invention for the determination of class-specific antibodies, as well as for the quantitation of such antibodies. Rheumatoid factors which are specific for immunoglobulin classes or sub-classes are known to exist.

In the present context, the expression "Fc receptor or Fc receptor-bearing cells" refers to those Fc receptor or Fc receptor-bearing cells that bind to clustered or aggregated antibody and not to monomeric or non-aggregated antibody. Thus, excluded from the scope of this expression are substances such as Protein A. The expression "rheumatoid factor-like antibody" as used herein, includes antibody that binds to another antibody or component of another antibody, only when the other antibody is aggregated, and may be understood with reference to the interaction between an IgM and a monovalent hapten, such as dinitrophenol (DNP), by way of example. By producing antibody to DNP, e.g. by monoclonal antibody techniques, it is possible to select an IgM producing clone having an affinity sufficiently low such that IgM would have no appreciable interaction with a single DNP molecule, but would react strongly under conditions where the DNP density affords IgM multivalent attachment. Thus, if a primary antibody (used in certain immune analyses) were moderately conjugated with DNP, it would have no interaction with the IgM anti-DNP, but would react when the former forms complexes with its specific antigen. Such rheumatoid factor-like antibodies are useful in the practice of the present invention.

The aforementioned immunospecific factors may be obtained by procedures known to those skilled in the art. For example, Clq may be purified from human serum according to the procedure described by Yonemasu et al., Journal of Immunology, Vol. 106, pp. 304–13 (1971). Rheumatoid factor may be isolated according to the procedures of Agnello, Manual of Immunology, 2nd Ed., American Society of Microbiology, Washington, D.C., pp. 170–85 (1980).

Immobilization of non-immunospecific factor may be achieved by chemical bonding or physical adsorption to a suitable support, e.g. microtiter plates. The appropriate procedure for immobilization will depend on the nature of the specific substance being immobilized.

Performance of the assay of the invention is facilitated by employing reagents, e.g. antigen, antibody or hapten, associated with a detectable label, for ready determination of the increase or decrease in the degree to which the complexes formed in the assay are bound to the test device. Any of the labels normally employed in immunoassays, such as enzymes, radioisotopes and fluorescent or phosphorescent substances may be used for this purpose. Coupling of the labels to the reagents may be accomplished by various procedures well-known to those skilled in the art. Of course the conditions employed for coupling label to reagent must be selected such that the immunological activity of the reagent and the function of the label are not significantly diminished.

Determination of the degree to which immune or formed complexes become bound to the test device, is accomplished by means of what is effectively an immunoprecipitation curve. In the case of immunological substances, for example, the curve is constructed over a range of compositions of immune complexes, which range includes compositions in which the amount of the immunological substance and the amount of the immunospecific conjugate are in substantial equivalence, compositions in which the amount of the immunological substance is in substantial excess of the amount of the immunospecific conjugate, and compositions in which the amount of the immunospecific conjugate is in substantial excess of the amount of the immunological substance. In this way, selected working limits for any desired assay are determinable within the aforesaid range of compositions of the immune complexes or formed complexes.

As will appear below, the selected working limits for assaying antigens, antibody and haptens generally encompass the region between equivalence and far antigen excess on the immunoprecipitation-like binding curve; however, the starting point for the selected working limit is different for antigen and hapten assays (at or near the equivalence point), than it is for antibody assays (in far antigen excess).

Construction of the standard assay or calibration curve is done in the usual way by plotting the relative degree of immunochemical binding of the immune complexes or formed complexes to the test device, employing a reference system comprising varying concentrations of the substance being assayed and a fixed concentration of the immunospecific conjugate or multivalent binding partner. In the case of assays for bindable substances, such as haptens, the reference system also includes a fixed concentration of a multivalent form of the bindable substance. In either case, the composition of immune complexes or formed complexes selected should be within the selected working limits previously established.

In preparing the test systems for assaying immunological substances or bindable substances, conditions are selected to produce a known degree of binding between the complexes formed and the non-immunospecific factor component of the test device. An addition of immunological substance or bindable substance, which disturbs or changes the composition (antigen/antibody ratio) or size of the complexes, alters the degree of binding of the complexes to the test device in a way which can be quantitatively determined. In other words, the determination of specific antigen, specific antibody, hapten or hapten-like substances, according to the present invention results from the optimization or diminution of binding between the complexes and insolubilized non-immunospecific factor.

In the case of specific antigen determinations, the test system is prepared with immune complexes formed at or near the equivalence ratios, producing optimal interaction with the non-immunospecific factor on the test device. Addition of test antigen to such a system shifts the equilibrium toward a condition of antigen excess, and in so doing, alters the antigen/antibody ratio of the complexes. This results in diminished binding of the complexes to the non-immunospecific factor. By providing one of the reagents with an appropriate label, the degree to which binding of the complex to the non-immunospecific factor is diminished may be readily quantitated.

In assaying for multi-determinant antigen when added unlabeled antigen drives the system to antigen excess, a defined mixture of antibodies directed against individual determinants and of equal binding affinity and concentration may be advantageous. That is because the ratios of all determinant-antibody pairs will vary similarly, in contrast to the situation that exists when anti-determinant antibodies are at different levels. This advantage may be achieved by using appropriate mixtures of monoclonal antibodies.

For specific antibody determinations, the test system is prepared in far antigen excess, with very little immune complex binding to the non-imunospecific factor. Addition of test antibody to the system alters the antigen/antibody ratio of the complexes in such a way as to shift the equilibrium of the system towards equivalent ratios of antigen and antibody, and consequently increases interaction and subsequent binding to the non-immunospecific factor on the test device. The shift toward optimal antigen/antibody ratios resulting in increased binding may be used to measure the quantity of specific antibody in a given test sample. Again, this is achieved simply by labeling one of the reagents, preferably antigen.

An alternative procedure for determining specific antibody involves establishing the lowest concentration of immune complexes (with antigen and antibody at equivalence) that can be detected by binding to non-immunospecific factor on the test device. Under such conditions, if an appropriate quantity of antigen is present in the system, such that when the lowest amount of detectable antibody is added the system shifts toward equivalent antigen/antibody ratios, then there is no need to have added specific antibody in the system initially. Thus, antibody determinations may conveniently be performed using an amount of antigen which corresponds to antigen excess for the lowest level of detectable antibody.

Since detection of specific antibodies according to the invention depends on immune complex formation, which, in turn requires multi-determinant antigens, it may be necessary in certain instances to prepare an antigen conjugate which assures multivalency. This need may arise in the detection of anti-viral antibodies, because viral proteins are known to have confined regions of antigenicity or "antigenic hotspots". Thus, when a virus is disrupted, the resultant individual virus proteins may only contain one or two determinants per molecule. In such situations, this low antigenic valency would not be expected to result in immune complexes of sufficient size or composition to interact With the aforementioned non-immunospecific factors. However, by appropriate cross-linking of viral proteins to each other, or to a reporter molecule, such as an enzyme, it is possible to construct a soluble macromolecular complex which has the requisite antigenic multivalency to form appropriate immune complexes when reacted with specific antibodies. Generally, the resultant cross-linked viral protein will have a non-naturally occurring form. The use of this approach in concert with viral protein prepared by recombinant DNA techniques affords the opportunity of determining specific antibody response to different viral proteins, e.g. core or envelope.

The test system for haptens or bindable low molecular weight substances is also prepared using complexes formed at or near equivalent ratios. In this system, the reagents are a multivalent form of the hapten or bindable substance to be determined and its immunospecific antibody. Addition of test hapten to the system results in destruction of the formed immune complexes and consequently diminishes their interaction with the non-immunospecific factor on the test device.

Determinations of specific antigen, specific antibody and hapten are exemplified below. These examples describe the invention in further detail, including the manner and process of making and using it, and set forth the best mode contemplated by the inventor for carrying out the invention.

EXAMPLE 1

Assay of Human IgE

The procedure of the invention for assaying antigen was performed using a test system in which human IgE was the target substance.

The test device was prepared by coating ninety-six well microtiter plates with human Clq. Specifically, 60 $\mu$l of a buffered saline solution of Clq (70 $\mu$g/ml in PBS) was placed in each well. The plates were covered and incubated overnight at 4° C. Controls were prepared by placing 60 of a 1.0% bovine serum albumin (BSA) solution (in PBS) into the wells, which were also covered and incubated overnight at 4° C. After incubation, the solutions were removed from the wells, which were then washed three times with PBS. In order prevent non-specific binding, each well was filled with 200 $\mu$l of 1.0% BSA (in PBS) and incubated for 2 hours at room temperature. After two hours, the BSA was removed and the wells were again washed three times with PBS. After washing, excess moisture was allowed to drain from the wells.

Human IgE labeled with $I^{125}$ was prepared according to the iodogen method to a specific activity of $2.2 \times 10^6$ cpm/μg. Anti-human IgE in the form of an affinity-purified, lyophilized preparation (obtained from the National Institutes of Health) was diluted to a final concentration of 5 μg/ml (in PBS, containing 5μg/ml BSA. Varying amounts of the labeled IgE (*IgE) were allowed to interact with 250 ng quantities of the anti-IgE antibody and incubated for about two hours to allow formation of immune complexes to occur. After incubation, 50 μl of each immune complex sample was placed in the Clq-coated wells and the BSA-coated control wells. The wells were then covered and incubated for two hours at room temperature. After incubation, the wells were washed three times with PBS for removal of unbound immune complexes, and the individual wells were placed into counting tubes and counted for one minute each in a Nuclear Chicago gamma counter. Duplicate Clq-coated test wells and single BSA-coated control wells were run for each of the IgE amounts used.(Alternatively, immune complexes may be formed directly in Clq-coated microtiter wells and incubated for four hours.)

Total counts per minute (cpm) for each of the wells was determined by counting 10 μl of the immune complex samples and multiplying by five to obtain the cpm/50 μl of immune complex loaded into each well. The cpm determined for the BSA-coated control well was subtracted from the cpm determined for each duplicate Clq-coated well receiving the same amount of IgE, and the resulting cpm values were averaged. The data obtained are set forth in Table A below. The percentage of immune complex bound to the Clq-coated test well for each level of added IgE may be obtained by dividing the average ($\overline{X}$) cpm determined by the cpm/50 μl of immune complex.

TABLE A

| ng*IgE | cpm Test Well | cpm Control Well | cpm/50 μl Immune Complex | $\overline{X}$ cpm Test Minus Control |
|---|---|---|---|---|
| 0.5 | 1230 | 93 | 3462 | 1153 |
|  | 1262 |  |  |  |
| 1.0 | 1949 | 130 | 6016 | 1933 |
|  | 2177 |  |  |  |
| 2.0 | 3008 | 171 | 9694 | 2857 |
|  | 3047 |  |  |  |
| 3.0 | 4280 | 153 | 13468 | 3993 |
|  | 4011 |  |  |  |
| 5.0 | 6751 | 286 | 16338 | 5770 |
|  | 5360 |  |  |  |
| 10.0 | 12104 | 345 | 30605 | 11827 |
|  | 12240 |  |  |  |
| 20.0 | 11895 | 715 | 35929 | 11753 |
|  | 13040 |  |  |  |
| 50.0 | 25723 | 1366 | 82223 | 26680 |
|  | 30368 |  |  |  |
| 80.0 | 18118 | 1665 | 134306 | 17564 |
|  | 20339 |  |  |  |
| 100.0 | 20551 | 1234 | 178462 | 17757 |
|  | 19431 |  |  |  |
| 150.0 | 8296 | 1167 | 254313 | 6428 |
|  | 6894 |  |  |  |

Figure 1:
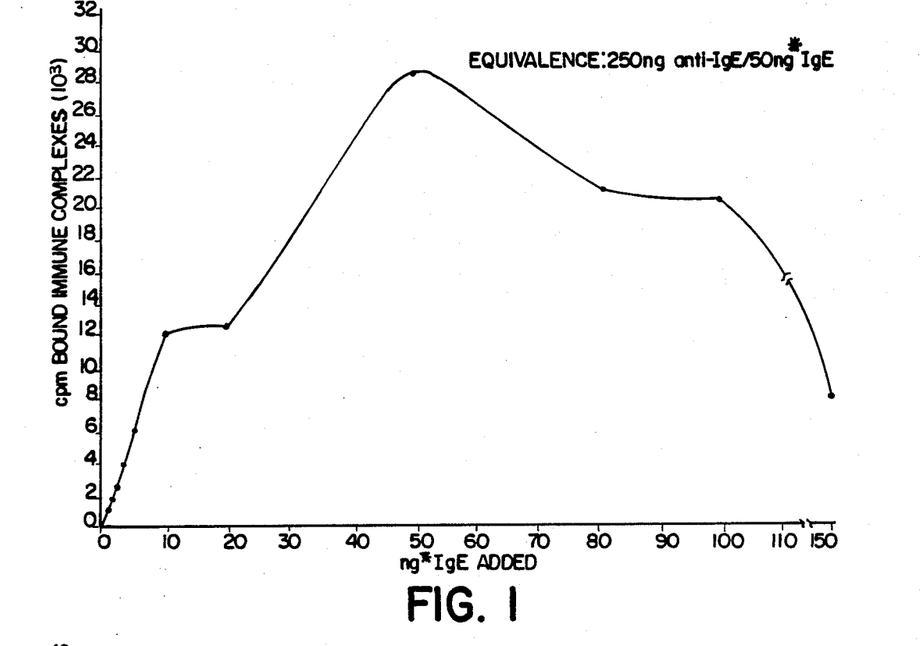
FIG. 1 is an immunoprecipitation-like binding curve in which the relative amount of immune complex bound to the test device is plotted as a function of the addition of increasing amounts of IgE in the presence of a fixed amount of anti-IgE antibody.

The average cpm for the immune complexes bound to the test wells was plotted against the amount of *IgE added at each level and is graphically represented in FIG. 1.

FIG. 1 shows that as the equivalence ratio of anti-IgE antibody to IgE is reached increasing amounts of immune complex are bound to the Clq-coated wells. The maximum binding of immune complexes to Clq-coated wells occurs at the equivalence ratios of antibody and antigen. Immune complexes formed in antibody excess (left had side of curve in FIG. 1) and immune complexes formed in antigen excess (right hand side of curve in FIG. 1) bind decreasing amounts of immune complexes, with increasing distance from the equivalence point.

Experiments of this type were repeated several times with dilutions of the antibody and antigen mixtures. These experiments demonstrate that this system is sensitive at the 1 ng/ml range of antigen (IgE).

The ability of this system to detect unlabeled d antigen via competitive immunoassay was established by the following test.

Figure 2:
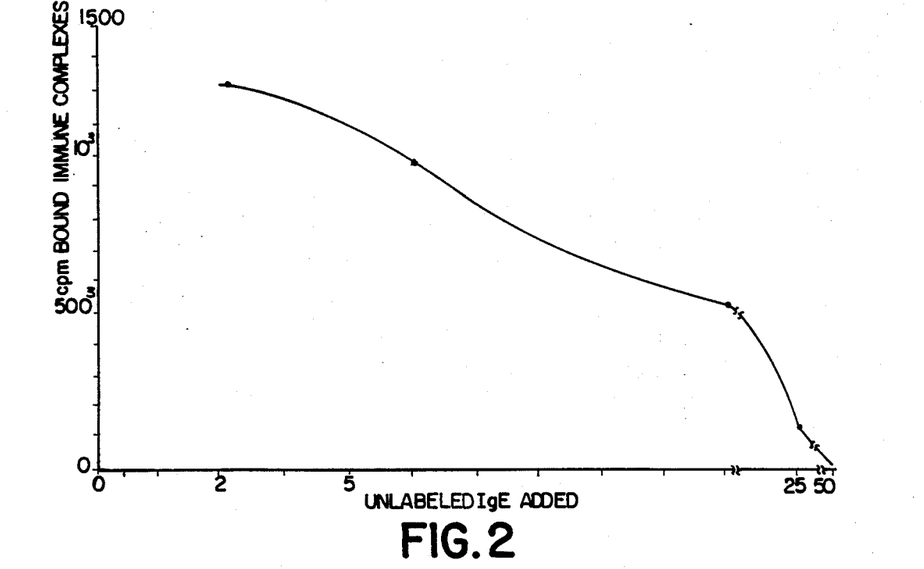
FIG. 2 is a standard curve, or calibration curve, which is constructed between working limits established by the immunoprecipitation-like curve of FIG. 1. and produced by plotting bound immune complex as a function of varying known amounts of IgE introduced into the test system.

Immune complexes comprising anti-IgE antibody and *IgE were formed at the equivalence point (which for this system was determined to be 25 ng anti-IgE antibody: 5 ng *IgE) in the presence of varying amounts of unlabeled IgE. The samples of immune complex were allowed to equilibrate for two hours at room temperature. 50 μl of the immune complex solution was then placed into Clq-coated test well and BSA-coated control wells as described above and incubated for four hours at room temperature, After incubation, the wells were washed three times with PBS to remove unbound immune complexes and the wells were counted. The cpm of the immune complexes bound to the test wells were plotted against the different levels of IgE and is graphically represented in FIG. 2. As can be seen in FIG. 2, as increasing amounts of unlabeled IgE are added, the amount of immune complex bound to the Clq-coated wells decreases in proportion to the amount of unlabeled IgE added. The standard curve of FIG. 2 serves as the reference in determining the amount of IgE present in test samples assayed utilizing this test system.

The above-described test was repeated with immune complexes formed at two and at four times *IgE excess, in order to determine the most sensitive region of the curve of FIG. 1. The data from these experiments indicates that the curve is most sensitive to the addition of unlabeled IgE in the region of slight Ag excess.

EXAMPLE 2

Assay of Anti-Horse Radish Peroxidase Antibody

The test system and procedure for assaying antibody according to this invention were used for the determination of anti-horse radish peroxidase (HRP) antibody.

A test device in the form of a ninety-six well microtiter plate was prepared essentially as described in Example 1, above. Rabbit antibody to HRP was raised by injection of rabbits with HRP in Freund's adjuvant. The rabbit antisera was collected, heat decomplemented at 56° C. for thirty minutes, tested by precipitation analysis and found to contain 460 μg specific anti-HRP/ml. Purified HRP was obtained from Sigma Chemical Co.

In preparing the test system, a fixed amount of anti-HRP (3 μg/ml) was incubated with varying amounts of added HRP ranging from 60 ng to 2700 ng/ml. 250 μl of the resultant immune complexes were placed in the Clq-coated test wells and incubated for 4 hours at room temperature. Two sets of controls were used in this experiment, namely, wells coated with BSA and wells containing antigen only. After incubation, the test wells were washed three times with PBS to remove unbound complexes and the HRP activity of the wells was determined. The enzyme activity determination was made using, as substrate and co-substrate, respectively, a 0.5 mM solution of 2,2'-azinolbis (3-ethyl-benythiazoline) sulfonic acid (ABTS) and 0.05 mM hydrogen peroxide ($H_2O_2$) dissolved in a buffer comprising 0.1M sodium chloride and 0.1 M sodium acetate at pH 4.4.

Enzyme incubation with substrate was carried out for 20 minutes at room temperature, with constant, gentle mixing on a rotator table. After incubation the microtiter plate was placed in an Intermed immunoreader and the optical-density at 405 nm and 490 nm was measured. A substrate only well was included on the plate in order to achieve the proper setting of the instrument.

Figure 3:
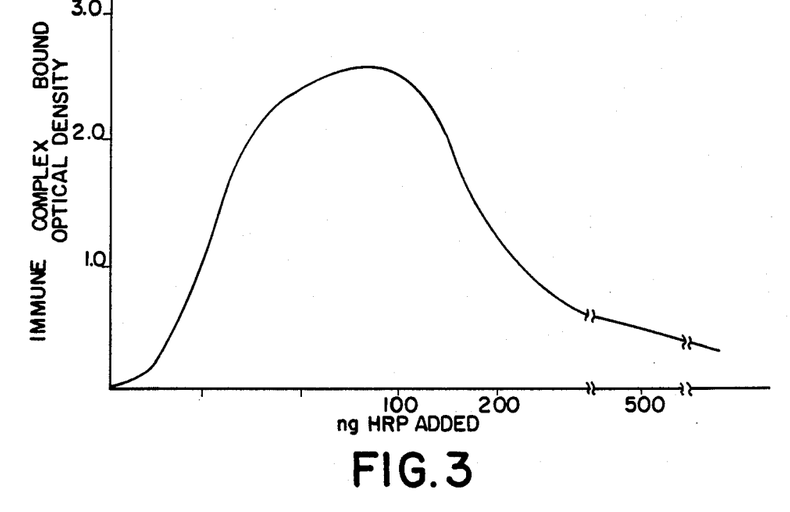
FIG. 3 is an immune complex binding curve in which the relative amount of immune complexes bound to the test device is plotted as a function of varying concentrations of horse radish peroxidase in the presence of a fixed amount of rabbit anti-peroxidase.

The equivalence ratio of the immune complex components was determined to be approximately 125 ng HRP: 750 ng anti-HRP. This value corresponds to the maximum amount of immune complex bound to the test wells as shown in FIG. 3 which is a graphical representation of the enzyme activity obtained as a result of this test.

Figure 4:
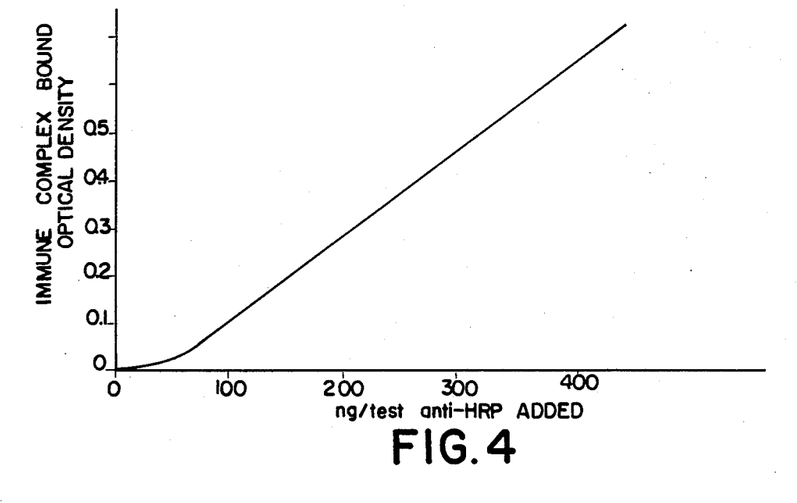
FIG. 4 is a standard curve, which is constructed between working limits established by the plot of FIG. 3, and produced by plotting bound immune complexes as a function of varying known concentrations of rabbit anti-peroxidase introduced into the test system.

FIG. 4 is the graphical representation of the data obtained when HRP fixed at 100 ng was incubated in Clq-coated wells with increasing amounts of anti-HRP added. FIG. 4 shows that as more anti-HRP antibody is added increasing amounts of immune complex bind to the Clq coated wells. The standard curve of FIG. 4 is used as a reference in determining the amount of anti-peroxidase antibody present in test samples assayed using this test system.

Figure 5:
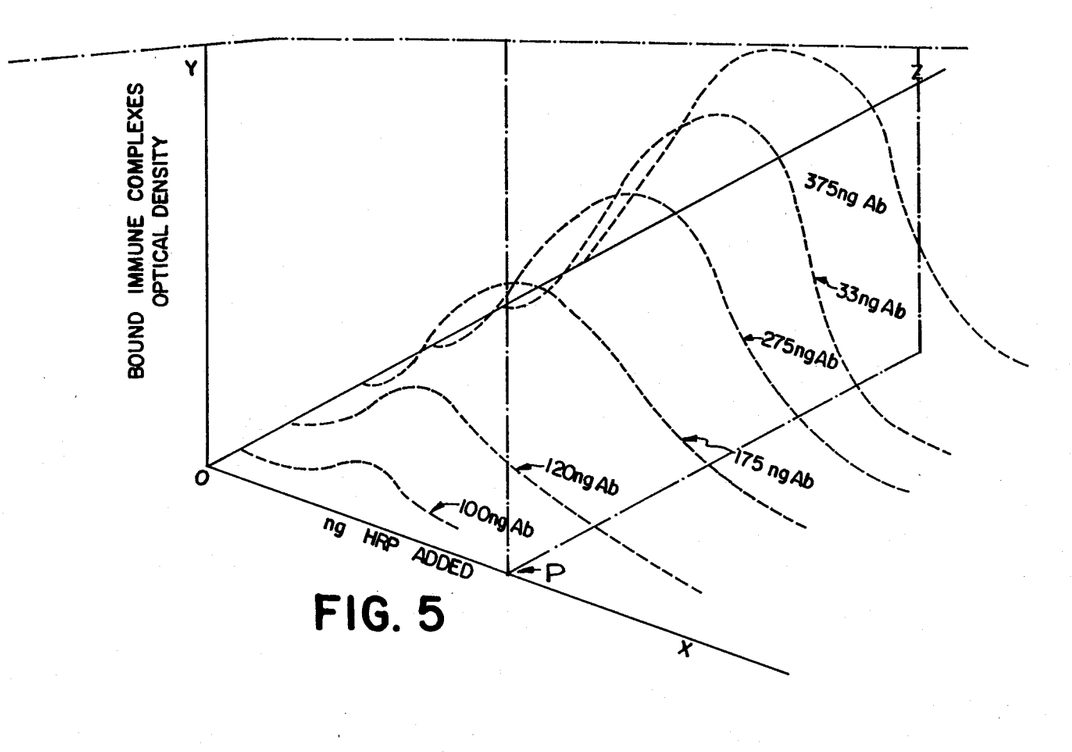
FIG. 5 is a three-dimensional representation of immune complex binding, also based on working limits established by the plot of FIG. 3, as a function of variable horse radish peroxidase concentrations and rabbit anti-peroxidase concentrations. The series of curves shown in FIG. 5, which correspond to varying rabbit anti-peroxidase concentrations, may be used to arrive at the standard or calibration curve for this test system, i.e.

Tests of the sort described above by which the plot of FIG. 3 was generated were repeated using different, fixed amounts of anti-HRP. From these tests, a series of curves was generated, as appear in FIG. 5 for the different amounts of anti-HRP used. Specifically, FIG. 5 depicts curves for six different antibody concentrations. It should be understood, however, that additional antibody curves may be generated, and an infinite set or family of such curves representing all antibody concentrations of interest will form a surface generally having the shape of a truncated hyperbolic paraboloid.

From FIG. 5 it will be seen that at the lowest concentration of anti-HRP employed, there is some level of excess HRP at which complex binding occurs (see point P on X-axis in FIG. 5), as indicated by HRP bound in the formed immune complex. After considering FIG. 5, it will be recognized by those skilled in the art that for the same level of HRP (corresponding to point P), higher levels of anti-HRP bind more HPR in immune complexes to the Clq-coated test device. Accordingly, it will be appreciated that one may generate from the surface resulting from such a family of curves, for virtually any antibody-antigen system, a plot of antigen bound to the test device as a function of antibody added, simply by passing a plane (such as represented by the dot and dashed line in FIG. 5) through the X-axis at some given level of antigen, the plane being substantially parallel to the plane of the y-z axes. The line formed by the intersection of such a plane With the surface which would result from an infinite series of curves like those shown in FIG. 5 gives the curve of antigen bound versus antibody added. As one would expect, such a curve generally corresponds to one generated experimentally, such as shown in FIG. 4.

EXAMPLE 3

Assay of Dinitrophenol

The test system and procedure for assaying hapten according to this invention were used in determined dinitrophenol (DNP).

The test device employed for this inhibition of binding assay was prepared generally in the manner described in Example 1, above. The multi-valent form of the hapten was DNP alkaline phosphatase. (DNP-AP). The multi-valent binding partner was antibody raised in rabbits by immunization with DNP hemocyanin, and recovered using conventional techniques.

In preparing the test system, varying amounts of DNP-AP, ranging from 1 to 100 µg/ml, were added to a fixed amount of the antibody (approx. 50 µg/ml in PBS) and incubated. 50 µl of the formed complexes were placed in the Clq-coated test wells and incubated for three hours. BSA-coated control wells were used in this example. After incubation, the wells were washed three times with PBS to remove unbound formed complexes, and the enzyme activity of the wells was determined using 3 mM p-nitrophenyl phosphate in 1M diethanolamine buffer (pH 9.8), at 100 µl/well. Optical density at 405/490 nm was measured, using an Intermed immunoreader.

Figure 6:
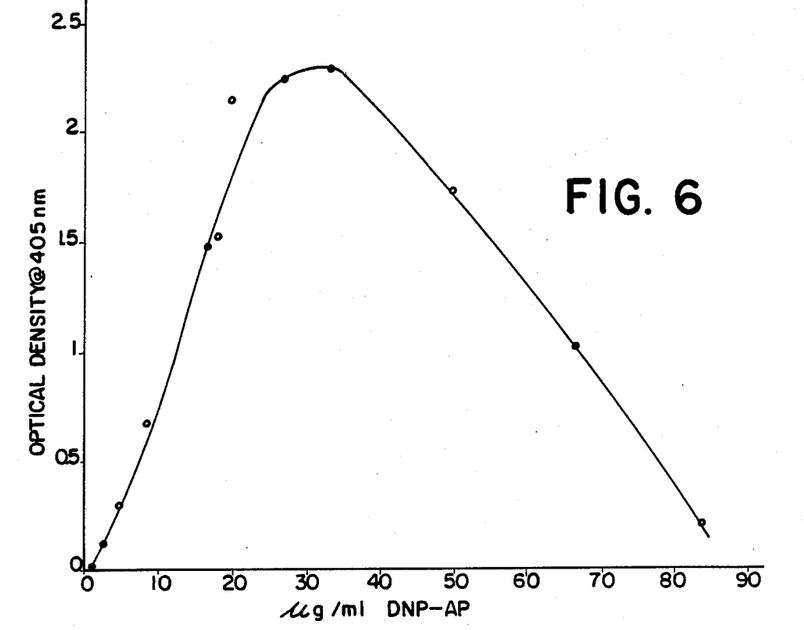
FIG. 6 is an immunoprecipitation-like binding curve in which binding of formed complexes to the test device is plotted as a function of varying concentrations of dinitrophenol conjugated to alkaline phosphatase.

The equivalence ratio of the formed complex components was determined to be 1.66 µg DNP-AP: 2.5 µg anti-DNP. A graphical representation of the enzyme activity obtained as a result of this test is provided in FIG. 6, which shows the maximum amount of formed complex bound to the test device occurring at about 30 µg/ml of added DNP-AP.

A test system was then provided consisting of a fixed amount of anti-DNP, (50 µg/ml), a near equivalent amount of DNP-AP (30 µg/ml) and increasing amounts of monovalent δDNP lysine, varying between 9 and 600 ng/ml. Controls were used comprising only DNP-AP and free DNP.

The test device employed in this test system was a Clq or BSA-coated ninety-six well microtiter plate. 50 µl of formed complex—DNP mixtures or control mixtures were deposited in the wells of the test plate. The test plate was then allowed to incubate for about three hours at room temperature. After incubation, the test plate was washed three times with PBS to remove unbound formed complexes. The enzyme activity of the wells was then determined according to the procedure described in Example 3, above.

Figure 7:
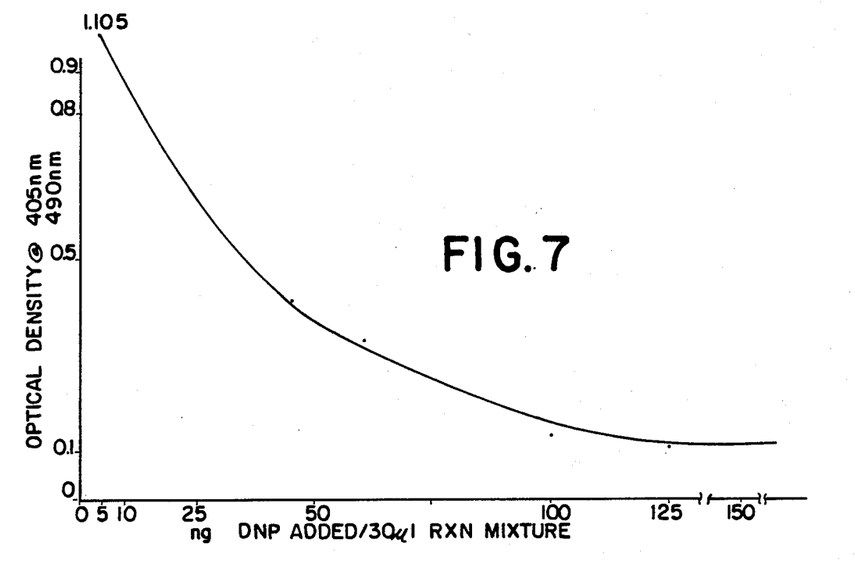
FIG. 7 is a standard curve constructed between working limits established by the curve of FIG. 6. The curve of FIG. 7 is generated by plotting bound formed complexes as a function of varying known concentrations of dinitrophenol introduced into the test system.

The enzyme activity determinations are represented graphically in FIG. 7, which indicates that monovalent DNP causes inhibition of the formed complexes resulting in the decreased coupling of formed complexes to the insolubilized Clq. The standard curve of FIG. 7 is used as a reference in determining the amount of DNP present in test samples assayed using this test system.

This particular procedure has extremely broad application since many commonly assayed drugs and biological materials are hapten-like in nature.

While the various aspects of the present invention have been described and exemplified above in terms of certain preferred embodiments, various other embodiments may be apparent to those skilled in the art. For example, the assay may be used for the detection of a wide range of biological materials in addition to IgE, HRP or DNP, such as the antigens HTLV-III, rubella, chlamydia, theophylline, phenytoin, primadone and cyclosporine and the corresponding antibodies with which these substances interact immunospecifically. The invention is, therefore, not limited to the embodiments specifically described and exemplified, but is capable of variation and modification without departing from the scope of the appended claims.

What is claimed is:

1. A process for preparing an immunoassay for quantitatively assaying a biological material for an immunological substance by means of immunochemical binding of immune complexes to insolubilized non-immunospecific factor having binding affinity for said complexes, which are composed of said immunological substance and an immunospecific conjugate which interacts specifically with said immunological substance, the degree of immunochemical binding of said immune complexes to said insolubilized non-immunospecific factor being a function of composition of said immune complexes and representable by an generally bell-shaped binding curve established over a range of compositions of said immune complexes, said range including compositions in which the amount of said immunological substance and the amount of said immunospecific conjugate are in substantial equivalence, in which the amount of said immunological substance is in substantial excess of the amount of said immunospecific conjugate, and in which the amount of said immunospecific conjugate is in substantial excess of the amount of said immunological substance, said process comprising the steps of:
   a. providing a test device comprising said insolubilized non-immunospecific factor;
   b. establishing selected working limits for said immunoassay within said range of compositions of said immune complexes;
   c. constructing a standard assay curve by plotting relative degree of immunochemical binding of said immune complex to said test device, said immune complex being formed in a reference system comprising varying concentrations of the immunological substance and a fixed concentration of the immunospecific conjugate of said substance, the composition of complexes resulting from said immunological substance and immunospecific conjugate being within the selected working limits of step b; and
   d. providing a test system comprising said test device, said immunospecific conjugate and said immunological substance, the amount of said immunospecific conjugate being substantially equivalent to said fixed concentration of immunospecific conjugate, and the amount of said immunospecifically determinable substance being appropriate to produce a known degree of immunochemical binding corresponding to a predetermined point on said standard assay curve, thereby enabling quantitative assaying of biological material for said immunological substance.

2. A process for assaying a biological material for an immunological substance using an immunoassay prepared as in claim 1, said process comprising the steps of:
   a. adding a sample of said biological material suspected of containing said immunological substance to the test system of claim 1;
   b. measuring any deviation from the known degree of immunochemical binding caused by the addition to said test system of any immunological substance present in said biological material; and
   c. determining the amount of immunological substance present in said biological material, based on said deviation from the known degree of immunochemical binding measured in the measuring step, by reference to the standard assay curve of claim 1.

3. A process as claimed in claim 2, wherein the non-immunospecific factor is selected from the group consisting of Clq, rheumatoid factor, rheumatoid factor-like antibody, and Fc receptor or Fc receptor-bearing cells.

4. A process as claimed in claim 2, wherein the respective amounts of said immunospecific conjugate and said immunological substance present in said test system are such as to form immune complexes, the composition of which is within the region corresponding to substantial equivalence between said immunological substance and said immunospecific conjugate on said standard assay curve.

5. A process as claimed in claim 4, wherein said immunological substance or said immunospecific conjugate has associated therewith a detectable label selected from the group consisting of an enzyme, a radioisotope, or a fluorescent or phosphorescent substance.

6. A process as claimed in claim 5, wherein the relative amount of said label present on said test device provides the measure of the deviation from the known degree of immunochemical binding.

7. A process as claimed in claim 4, wherein the non-immunospecific factor comprises Clq.

8. A process as claimed in claim 7, wherein said immunological substance comprises, multivalent antigen, and said immunospecific conjugate comprises complement-fixing antibody which reacts specifically with said multivalent antigen, and as the amount of said antigen increases in the range of compositions wherein said antigen is present in substantial excess of said antibody, the degree of interaction between said immune complexes and said Clq is decreased.

9. A process as claimed in claim 8, wherein said complement-fixing antibody comprises a mixture of antibodies directed against individual determinants of said multivalent antigen, the antibodies in said mixture being of substantially equal binding affinity and concentration.

10. A process as claimed in claim 9 wherein said antibody mixture comprises monoclonal antibodies.

11. A process as claimed in claim 8, wherein said antigen or antibody has associated therewith a detectable label selected from the group consisting of an enzyme, a radioisotope, or a fluorescent or phosphorescent substance.

12. A process as claimed in claim 11, wherein the amount by which the label present on said test device decreases provides the measure of deviation from the known degree of immunochemical binding.

13. A process as claimed in claim 12, Wherein said label is associated with said antigen.

14. A process as claimed in claim 11, wherein said multivalent antigen is selected from the group consisting of IgE, complement components, albumin or ferritin and said antibody is the corresponding antibody with which said antigen interacts specifically.

15. A process as claimed in claim 2, wherein the amount of said immunospecific conjugate present in said test system constitutes an excess relative to said immunological substance, for the lowest level of immunological substance which is capable of binding to said test device, when present with a substantially equivalent amount of said immunospecific conjugate.

16. A process as claimed in claim 2, wherein the respective amounts of said immunospecific conjugate and said immunological substance present in said test system are such as to form immune complexes, the composition of which is within the region wherein said immunospecific conjugate is in substantial excess of said immunological substance on said standard assay curve.

17. A process as claimed in claims 15 or 16, wherein the non-immunospecific factor is selected from the group consisting of Clq, rheumatoid factor, rheumatoid factor-like antibody and Fc receptor or Fc receptor-bearing cells.

18. A process as claimed in claims 17, wherein said immunological substance or said immunospecific conjugate has associated therewith a detectable label selected from the group consisting of an enzyme, a radioisotope, or a fluorescent or phosphorescent substance.

19. A process as claimed in claim 18, wherein the relative amount of said label present on said test device provides the measure of the deviation from the known degree of immunochemical binding.

20. A process as claimed in claim 17, wherein the non-immunospecific factor is Clq.

21. A process as claimed in claim 20, wherein said immunological substance is complement-fixing antibody and said immunospecific conjugate is antigen with which said antibody interacts specifically.

22. A process as claimed in claim 21 wherein said antigen comprises a multi-determinant antigen formed by cross-linking individual viral proteins.

23. A process as claimed in claim 22 wherein said viral proteins are cross-linked to one another.

24. A process as claimed in claim 22 wherein said viral proteins are cross-linked to a reporter molecule.

25. A process as claimed in claim 24 wherein the reporter molecule is an enzyme.

26. A process as claimed in claim 21, wherein said antigen or antibody has associated therewith a detectable label selected from the group consisting of an enzyme, a radioisotope, or a fluorescent or phosphorescent substance.

27. A process as claimed in claim 26, wherein the amount by which the label present on said test device increases provides the measure of the deviation from the known degree of immunochemical binding.

28. A process as claimed in claim 27, wherein said label is associated with said antigen.

29. A process as claimed in claim 26, wherein said antibody is anti HTLV-III and said antigen is HTLV-III protein.

30. A process as claimed in claim 26, wherein said antibody is anti-rubella, and said antigen is rubella.

31. A process as claimed in claim 26, wherein said antibody is anti-chlamydia, and said antigen is chlamydia.

32. A process for preparing an assay for quantitatively assaying a biological material for a monovalent bindable substance by means of inhibition of binding of formed complexes to non-immunospecific factor having binding affinity for said complexes, which are composed of a multivalent form of said bindable substance and a multivalent binding partner which binds said bindable substance specifically, the degree of binding of said formed complexes to said non-immunospecific factor being a function of composition of said formed complexes and representable by generally bell-shaped binding curve established over a range of compositions of said formed complexes, said range including compositions in which the amount of said multivalent form of said bindable substance and the amount of said multivalent binding partner are in substantial equivalence, in which the amount of said multivalent form of said bindable substance is in substantial excess of the amount of said multivalent binding partner, and in which the amount of said multivalent binding partner is in substantial excess of the amount of said multivalent form of said bindable substance, said process comprising the steps of:
 a. providing a test device comprising said insolubilized non-immunospecific factor;
 b. establishing selected working limits for said assay within said range of compositions of said formed complexes;
 c. constructing a standard assay curve by plotting relative degree of coupling of said formed complexes to said test device, said formed complexes being formed in a reference system comprising a fixed concentration of said multivalent binding partner, a fixed concentration of said multivalent form of said bindable substance, the composition of complexes resulting from said multivalent binding partner and said multivalent form of said bindable substance being within the selected working limits of step b, and varying concentrations of said bindable substance; and
 d. providing a test system comprising said test device, said multivalent binding partner, said multivalent form of said bindable substance and said bindable substance, the respective amounts of said multivalent binding partner and said multivalent form of said bindable substance being substantially equivalent to said fixed concentration thereof, and the amount of said bindable substance being appropriate to produce a known degree of coupling corresponding to a predetermined point on said standard assay curve, thereby enabling quantitative assaying of biological material for said bindable substance.

33. A process for assaying a biological material for a monovalent bindable substance using an assay prepared as in claim 32, said process comprising the steps of:
 a. adding a sample of said biological material suspected of containing said bindable substance to the test system of claim 32;
 b. measuring any deviation from the known degree of coupling caused by the addition to said test system of any bindable substance present in said biological material; and
 c. determining the amount of bindable substance present in said biological material, based on said deviation from the known degree of coupling measured in the measuring step, by reference to the standard curve of claim 32.

34. A process as claimed in claim 33, wherein the non-immunospecific factor is selected from the group consisting of Clq, rheumatoid factor, rheumatoid factor-like antibody and Fc receptor or Fc receptor-bearing cells.

35. A process as claimed in claim 33, wherein the respective amounts of said multivalent binding partner and said multivalent form of said bindable substance present in said test system with said appropriate amount of bindable substance are such as to form complexes, the composition of which is within the region corresponding to substantial equivalence between said multivalent form of said bindable substance and said multivalent binding partner on said standard assay curve.

36. A process as claimed in claim 35, wherein said multivalent form of said bindable substance, said multivalent binding partner or said bindable substance has associated therewith a detectable label selected from the group consisting of an enzyme, a radioisotope, or a fluorescent or phosphorescent substance.

37. A process as claimed in claim 36, wherein the relative amount of said label present on said test device provides the measure of deviation from the known degree of coupling.

38. A process as claimed in claim 35, wherein the non-immunospecific factor is Clq.

39. A process as claimed in claim 38, wherein said bindable substance is a hapten and said multivalent binding partner is antibody which binds specifically to a multivalent form of said hapten.

40. A process as claimed in claim 39, wherein said multivalent form of said hapten, said antibody or said hapten has associated therewith a detectable label selected from the group consisting of an enzyme, radioisotope, or a fluorescent or phosphorescent substance.

41. A process as claimed in claim 40, wherein the amount by which the label present on said test device decreases provides the measure of deviation from the known degree of coupling.

42. A process as claimed in claim 41, wherein said label is associated with said multi-valent form of said hapten.

43. A process as claimed in claim 40, wherein said hapten is theophylline and said antibody is anti-theophylline.

44. A process as claimed in claim 40, wherein said hapten is phenytoin and said antibody is anti-phenytoin.

45. A process as claimed in claim 40, wherein said hapten is primadone, and said antibody is anti-primadone.

46. A process as claimed in claim 40, wherein said hapten is cyclosporine, and said antibody is anti-cyclosporine.

* * * * *

UNITED STATES PATENT AND TRADEMARK OFFICE
CERTIFICATE OF CORRECTION

PATENT NO. : 4,925,788

DATED : May 15, 1990

INVENTOR(S) : Paul A. Liberti

It is certified that error appears in the above-identified patent and that said Letters Patent is hereby corrected as shown below:

```
Column 8, line 40, delete "precipitation" and insert
    --precipitin--.
Column 12, line 22, delete "With" and insert --with--.
Column 14, line 56, delete "precipitation" and insert
    --precipitin--.
Column 15, line 62, delete "With" and insert --with--.
Column 17, line 19, after "by" delete --an--.
Column 18, line 32, before "said" delete --and--.
```

Signed and Sealed this

Twelfth Day of November, 1991

Attest:

HARRY F. MANBECK, JR.

*Attesting Officer*     *Commissioner of Patents and Trademarks*